United States Patent [19]

Jones

[11] 4,272,380

[45] Jun. 9, 1981

[54] SOLVENT FRONT DETECTION METHOD AND MANUFACTURE

[75] Inventor: Donald W. Jones, San Clemente, Calif.

[73] Assignee: Analytical Systems, Inc., Laguna Hills, Calif.

[21] Appl. No.: 75,347

[22] Filed: Sep. 13, 1979

[51] Int. Cl.³ .............................................. B01D 15/08
[52] U.S. Cl. ........................................ 210/658; 210/85
[58] Field of Search .................... 210/31 C, 85, 198 C

[56] References Cited

U.S. PATENT DOCUMENTS

| | | | |
|---|---|---|---|
| 3,046,779 | 7/1962 | Coleman | 210/198 C |
| 3,598,995 | 8/1971 | Inoue et al. | 210/198 C |
| 3,714,035 | 1/1973 | Jones | 210/198 C |
| 3,914,174 | 10/1975 | Fuchs | 210/198 C |
| 4,126,554 | 11/1978 | Rainin | 210/198 C |

*Primary Examiner*—John Adee
*Attorney, Agent, or Firm*—Bertram I. Rowland

[57] ABSTRACT

An improved method of thin layer chromatography and articles are provided for the detection of drugs involving extraction, concentration, transfer to a disc, development and detection. The method employs lipophilic dye containing disc shaped inserts impregnated with analytes or one or more standards. The discs are inserted in corresponding hollows on a thin layer chromatographic plate and eluted with a suitable solvent. As the solvent migrates, the dye is eluted from the disc and migrates as a spot with the solvent front which is thus visually developed with the dye.

6 Claims, No Drawings

SOLVENT FRONT DETECTION METHOD AND MANUFACTURE

BACKGROUND OF THE INVENTION

1. Field of the Invention

Thin layer chromatography is a versatile and economic method for the determination of a wide variety of drugs in physiological media. The field of thin layer chromatography has been extensively researched and many techniques and reagents have been developed for the detection of drugs. One such technique is exemplified in U.S. Pat. No. 3,714,035. This technique involves the scoring of the chromatograph adjacent one end to leave a plurality of openings in which discs may be introduced. One disc is impregnated with the analyte. In the other scored areas, one or more discs are introduced which have known amounts of specific drugs. By developing the sample and standards simultaneously on the same chromatograph, one can compare the migration rate of the sample spots to those of the standard spots, as well as their response to heat and/or chemical treatment. An accurate determination of whether or not a specific drug is present may thus be made.

However, in the course of the development of the chromatogram which may take anywhere from five minutes to well over an hour, it is essential to monitor the solvent front from time to time to determine if the chromatograms have developed sufficiently for the samples to be detected and identified as well as to prevent the solvent front from being eluted off the chromatographic plate. Current methods used for the purpose require the utilization of special or highly sophisticated equipment and/or sophisticated detection methods, as solvent fronts are usually very difficult to detect and follow visually. The method described herein provides for a visual monitoring of solvent fronts in thin layer chromatograph process whereby expensive and sometimes tedious detection systems and sophisticated technological know-how are eliminated.

2. Description of the Prior Art

Articles and texts of interest include Dole, et al. Detection of Narcotic Drugs, Tranquilizers, Amphetamines, Barbiturates in Europe, JAMA, 198, 349 (1966); Jones, et al. Drug Detection by TLC, Comparative Study, California Association of Criminologists, Menlo Park, California October 1973; Jones, et al. An Improved Method for the Detection of Phenothiazines, Annual Meeting, CAP-ASCP, Chicago, Illinois October, 1973; Davidow, et al. A Thin Layer Chromatographic Screening Procedure for Detecting Drug Abuse, The American Journal of Clinical Pathology, 38, 714 (1968). U.S. Pat. Nos. 3,914,174 and 3,496,102.

SUMMARY OF THE INVENTION

A method is provided for rapidly and accurately detecting the presence of a wide variety of basic amine, acidic, aromatic and neutral drugs, employing a thin layer chromatograph, whereby the migrating solvent front is monitored continuously or at will by means of a visually detectable dye. Disc shaped inserts are employed, which are blanks, or discs which are impregnated with one or more unknown samples or one or more standards, wherein at least one of these discs is impregnated with a lipophilic dye. The inserts are then placed in corresponding hollows scored on a chromatographic plate and the chromatograph developed according to prescribed methods. As the solvent system migrates on the chromatographic plate, the drugs impregnated on the discs are chromatographed and the dye quickly eluted from the discs to sharply define the solvent front.

DESCRIPTION OF THE SPECIFIC EMBODIMENTS

A chromatographic method is provided for rapidly determining acidic, aromatic, basic amine and neutral drugs. The method is normally concerned with the detection of a drug in a physiological sample, such as urine or serum, depending upon the drug of interest. The sample is introduced into an extraction vessel or zone containing salt (aqueous saturated $ZnCl_2$ for acidic and neutral drugs; combination of sodium chloride, sodium bicarbonate and sodium carbonate for basic and neutral drugs) and a halocarbon extractant solvent system. After agitating the vessel so as to enhance the transfer of the drug(s) to the organic extractant, the organic extractant is then transferred to a small evaporating dish of convenient size. In the evaporating dish is a small adsorbent disc which serves to adsorb the drug substantially completely. The transfer of the organic extractant to the adsorbing disc is carried out intermittently whereby substantially all of the solvent is evaporated before a subsequent addition, by maintaining the evaporating dish at a mildly elevated temperature. This method of evaporation results in a substantially complete transfer of any drugs contained in the organic extractant to the small adsorbent disc.

A thin layer chromatogram with a substantially insert support, normally glass fiber with alumina or silica gel as the adsorbant, is employed. The inert support should be such that it can withstand sulfuric acid treatment and does not interfere with the development of the chromatograph. The chromatographic plate has one or more scored areas which are aligned adjacent one end of the chromatograph. One of the scored areas is for receiving the sample adsorbent disc of the same composition as the chromatogram. The discs generally vary in size from about 1 to 5 mm in diameter. The other scored areas are used for introducing adsorbent discs which are employed as standards and have known amounts of specific drugs. Therefore, when the chromatograph is developed, the spots resulting from the sample disc can be compared to the spots resulting from the standard disc as to color and distance of migration ($R_f$), usually after appropriate treatment.

In accordance with the subject invention, the sample disc and/or the standard disc(s) are preimpregnated with a small amount of a lipophilic dye which is readily eluted from the disc by the eluting solvent. The amount of the dye in the disc varies widely depending upon the ease with which it is eluted, ease of visualization, and other relevant factors. Generally, solutions of the dye employed for impregnation have dye concentration in the range of from 1 to 20 mg/100 ml, more usually 2 to 10 mg/ml. The dye on the disc will generally be about 0.001 to 0.5 μg, usually about 0.005 to 0.025 μg, more usually about 0.01 to 0.015 μg.

Various lipophilic dyes which are soluble in the eluting solvent and which migrate with the solvent front may be used. Conveniently, dyestuffs in such classes as fat-soluble dyes (Colour Index: Solvent Dyes) metal complex dyestuffs which are soluble in organic solvents (CI: Disperse Dyes) or the like may be employed. Of particular interest are azo dyes. Exemplary of the useful dyestuffs are Oil red O 1-[(4-[xylylazo]xylyl)azo]-2-naphthol, Sudan IV Oil Red OB and Oil Blue A.

In the choice of dye factors that need to be considered are that it does not change the color or appearance of the chromatogram significantly, except at the solvent front, must not degrade the disc shelf-life, must not interfere with drug migration, must be eluted as a narrow band at the solvent front, and must be brilliant and readily observed at a distance of about 10 to 20'. Many dyes within the lipophilic classes fullfill these requirements and can be readily evaluated for their performance.

After inserting the dry adsorbent disc into the scored areas of the chromatograph, the chromatograph is in turn introduced into a chromatographic jar having a small amount of a suitable developing solution. As the developing solution moves up the chromatograph, it extracts and carries with it the dye as a discrete spot so that by following the migrating solvent front by means of the visually detectable dye, the development of the chromatograph is monitored as a function of time. The chromatograph is then removed from the jar and the solvent evaporated to leave a dry chromatograph. Depending on the drug or drugs of interest, the chromatograph is now treated according to prescribed methods which result in the visualization of specific spots. By comparing the spots of the sample as to size and color with spots of the standards, one can make a semi-quantitative determination of the approximate amount of the particular drug in the solvent.

The solvent systems employed will generally involve at least about 40 volumes, usually at least about 50 volume percent of a halocarbon, usually a chlorocarbon of from about 1 to 2 carbon atoms, for example, chloroform. Other materials which may be added individually or in combination, depending upon the nature of the drug, include alkanols of from 1 to 2 carbon atoms, for example, methanol, water, ammonium hydroxide and low molecular weight organic esters of fewer than six 6 carbon atoms, for example, ethyl acetate. Illustrative eluting solvents include: (1) 29 ml chloroform; 1 ml MeOH; 0.5 ml $H_2O$; 250 $\mu$l conc. $NH_4OH$; and (2) 1:1 chloroform: ethyl acetate.

The subject invention resolves the problem of solvent front detection. The presence of the dye in the disc is extremely convenient for the technician, since no extraneous solvent front markers are needed. It is found that during the chromatographic process, the dye rapidly elutes from the disc and is concentrated at the solvent front to clearly define the progress of the solvent front. As the chromatograph develops the dye migrates immediately to the solvent front, so that with the development of the chromatograph the solvent boundary becomes sharper and more distinct providing a further indicia of the progress of the chromatographic development.

Although the foregoing invention has been described in some detail by way of illustration and example for purposes of clarity of understanding, it will be obvious that certain changes and modifications may be practiced within the scope of the appended claims.

What is claimed is:

1. In a thin layer chromatographic method employing a chromatogram having a plurality of scored areas adjacent one end of said chromatogram and having inserted into said scored areas at least one disc impregnated with an analyte and at least one disc impregnated with a known organic compound, and eluting said analyte and said known compound with an eluting solvent, whereby said solvent, said analyte and said known organic compound migrate away from said discs, with said solvent defining a solvent front, the improvement which comprises, having a solvent elutable lipophilic dye impregnated into at least one of said discs, whereby said lipophilic dye migrates away from said disc said dye traveling with said solvent at said solvent front, wherein said solvent elutable lipophilic dye is present in said disc in sufficient amount to provide at said solvent front easy visual detection of said front.

2. A method according to claim 1, wherein said absorbent is silica gel or alumina, said disc is of from about 1 to 5 mm in diameter and said dye on said disc will generally be in an amount of from about 0.001 to 0.5 $\mu$g.

3. A method according to claims 1 or 2, wherein said solvent includes at least about 40 volume percent chloroform.

4. A method according to claim 3, wherein said dye is an azo dye.

5. A method according to claim 4, wherein said dye is 1-(4-(xylylazo)xylyl)azo)-2-naphthol.

6. A method according to claim 1, wherein all of said discs are impregnated with said dye.

* * * * *